United States Patent
Krasenics, Jr.

(10) Patent No.: US 6,646,560 B1
(45) Date of Patent: Nov. 11, 2003

(54) WINDOW FAN WITH RAIN SENSING CONTROL

(75) Inventor: Victor A. Krasenics, Jr., Orange, CT (US)

(73) Assignee: H. P. Intellectual Corp., Wilmington, DE (US)

(*) Notice: Subject to any disclaimer, the term of this patent is extended or adjusted under 35 U.S.C. 154(b) by 140 days.

(21) Appl. No.: 10/040,083

(22) Filed: Oct. 26, 2001

(51) Int. Cl.[7] ............................................. G08B 21/00
(52) U.S. Cl. ...................... 340/602; 340/604; 318/483; 73/170.17
(58) Field of Search ................. 340/602, 603, 340/604; 261/26, 129; 73/170.17, 170.21; 318/483

(56) References Cited

U.S. PATENT DOCUMENTS

| | | |
|---|---|---|
| 2,769,872 A | 11/1956 | Clark |
| 2,856,476 A | 10/1958 | Kaiser |
| 3,755,636 A | 8/1973 | Hill ........................ 200/61.05 |
| RE31,633 E * | 7/1984 | Lewis ........................ 34/13.8 |
| 4,578,995 A | 4/1986 | Meyer ........................ 73/171 |
| 4,692,751 A | 9/1987 | Upton et al. ............... 340/602 |
| 4,805,070 A | 2/1989 | Koontz et al. ............. 361/286 |
| 4,827,198 A | 5/1989 | Mueller et al. ............ 318/483 |
| 4,831,493 A | 5/1989 | Wilson et al. ............. 361/286 |
| 4,837,986 A | 6/1989 | Gagne ............................. 52/1 |
| 5,035,091 A | 7/1991 | Ebato ............................. 52/1 |
| 5,040,411 A | 8/1991 | Medzius ........................ 73/73 |
| 5,533,391 A | 7/1996 | Brade et al. ............. 73/170.19 |
| 5,598,146 A | 1/1997 | Schroder .................... 340/602 |
| 5,659,294 A | 8/1997 | Schroder .................... 340/602 |
| 5,780,718 A | 7/1998 | Weber ........................ 73/29.01 |
| 5,789,670 A | 8/1998 | Scherer et al. ........... 73/170.17 |
| 5,987,912 A * | 11/1999 | Flessner ...................... 62/407 |
| 6,147,753 A | 11/2000 | Koyama et al. .......... 356/237.3 |
| 2003/0034573 A1 * | 2/2003 | Mulvaney .................... 261/26 |

OTHER PUBLICATIONS

Radio Shack, Cat. No. 62–5019, Engineers's Mini-Notebook, 4 pages, 1995.

* cited by examiner

Primary Examiner—Julie Lieu
(74) Attorney, Agent, or Firm—Barry E. Deutsch

(57) ABSTRACT

A window fan assembly comprising a housing with openings therein for an air stream through the housing; at least one fan is mounted in the housing for generating the air stream through the openings of the housing; and a sensor connected to the housing, the sensor being disposed on the housing for detecting moisture particles associated with the air stream, upon the detection of a moisture particle of a predetermined size, the sensor causes an interruption of the air stream by stopping the fan operation.

16 Claims, 4 Drawing Sheets

WINDOW FAN WITH RAIN SENSING CONTROL

BACKGROUND OF THE INVENTION

1. Field of the Invention

The present invention relates to window fans, and, in particular, relates to devices for controlling the fan during inclement weather, especially during rain.

2. Brief Description of Related Developments

During raining weather, rain whether wind blown or otherwise may enter through a window having a window fan therein.

Thus, there exists a need for controlling the action of a window fan under inclement conditions.

SUMMARY OF THE INVENTION

In accordance with a first embodiment of the present invention a window fan assembly is provided. The window fan assembly comprises a housing with openings therein for an air stream through the housing. At least one fan is mounted in the housing for generating the air stream through the openings of the housing and a sensor is connected to the housing for detecting moisture particles associated with the air stream and upon the detection of a moisture particle of a predetermined size, the sensor causes interruption of the air stream by stopping the fan operation.

In accordance with a method of the present invention, a method is provided for controlling the fan operation in the present of moisture particles. The window fan has at least one fan in a housing with openings therein for an air stream during fan operation. A sensor is mounted in the window fan housing in close proximity to the openings for the air stream for sensing the presence of moisture particles therein. The sensor has a sensor circuit to control the fan operation by a sensor element having two separated conductive grid works, the grid works being separated by a predetermined distance. In the presence of moisture particles of a predetermined size, the sensor circuit interrupts fan operation to prevent the air stream from carrying the moisture particles through the fan housing.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
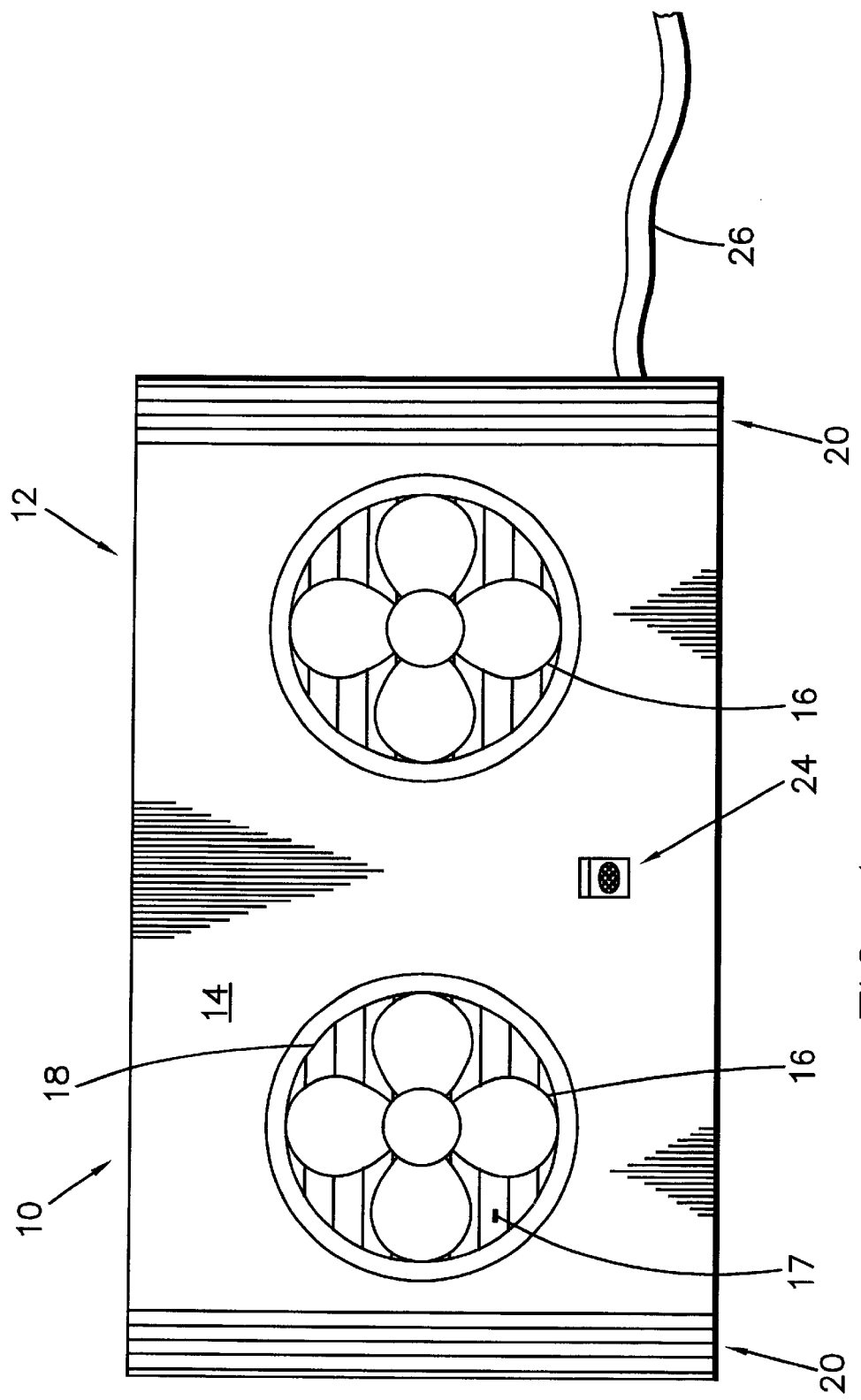
FIG. 1 is an elevation view of the window fan incorporating features of the present invention.

Referring to FIG. 1, there is shown a front view of a window fan 10 incorporating features of the present invention. Although the present invention will be described with reference to the embodiment shown in the drawings, it should be understood that the present invention could be embodied in many alternate forms of embodiments. In addition, any suitable size, shape or type of elements or materials could be used.

As shown in FIG. 1, the window fan 10 generally comprises a window fan with a housing designed and configured to fit within a window opening with one or more fan openings in the front and back walls. The fan section comprises a fan motor mounted in the housing with a fan blade thereon. The fan motor is controlled by a fan circuit providing one or more of the following features: controls to turn the fan motor on or off, change direction of the motor, or change the speed of the motor and a rain sensor device for controlling the fan motor in the presence of precipitation mounted to the front wall of the window fan housing. The rain sensor circuit has a controller for turning off power to the fan motor upon at least one raindrop contacting a grid work of conductive material; otherwise, the rain sensor circuit does not affect the electrical power to the fan motor.

Figure 4:
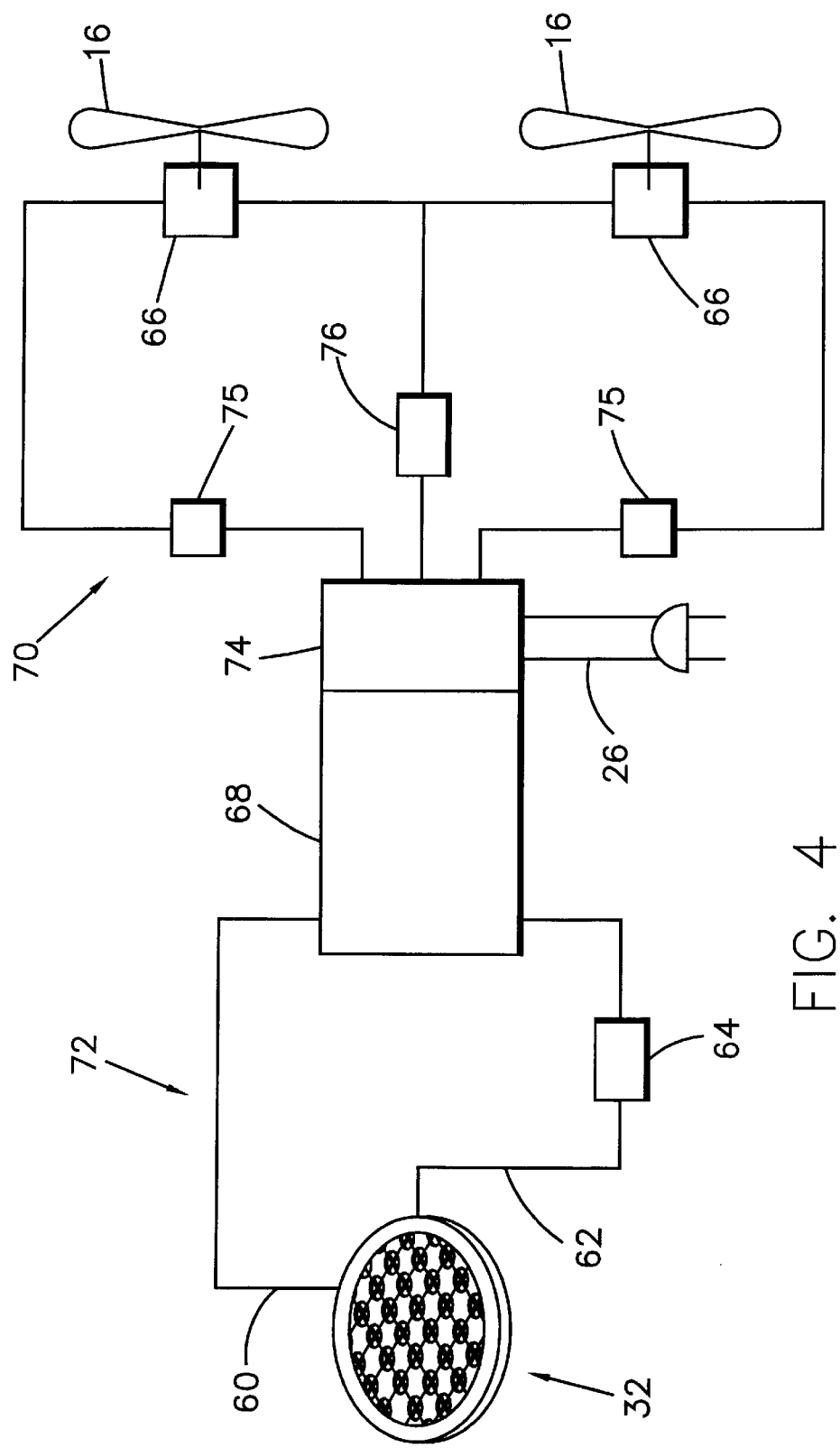
FIG. 4 is a schematic diagram of the circuit used to control the window fan of the present invention.

Referring to FIG. 1, a window fan 10 is shown by front view having a housing 12 of essentially rectangular configuration and made of plastic, metal or a combination of either. The housing 12 may have other configurations that are equally suitable, but FIG. 1 shows the housing 12 with a front wall 14. The back, sides, top and bottom walls are not shown. In the preferred embodiment, a pair of fan motors 66, FIG. 4, is mounted to the housing 12 with fan blades 16, mounted to the fan motors 66. In alternative embodiments, there may be any number of fans in the housing. For further controlling the flow of air, a rotating grill 18, for example, is mounted to the back wall. Adjustable accordion spacers 20 are mounted on the side walls for properly fitting the window fan 10 in the window opening, not shown. A rain sensor device 24 is positioned and mounted in the window fan 10. An appropriate line cord 26 is mounted to the housing 12 and provides power to the fan motors 66 and the rain sensor device 24.

Figure 3:
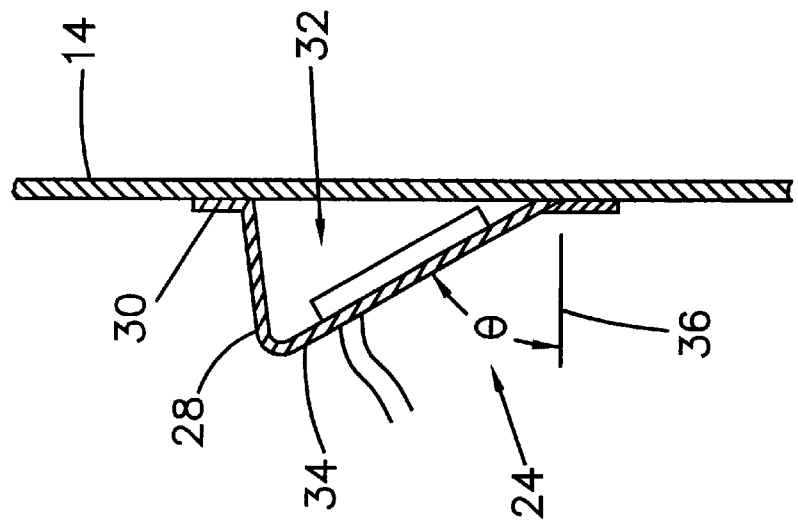
FIG. 3 is a partial cross sectional side view of the rain sensor device of the present invention mounted in a front wall of the housing of the window fan of FIG. 1.

The rain sensor device 24, FIG. 3, is shown in a cross-sectional side view mounted to the front wall 14 and facing to the outside of the window in the preferred embodiment. In this position, the rain sensor device 24 may be exposed to wind driven rain or to some of the rain that is being drawn into a fan opening 17. The rain sensor device 24 is generally mounted centered between the fan openings 17. In this location, the rain sensor device 24 may sense rain drops which may be drawn/enter in the fan opening 17. In alternative embodiments, the sensor device 24 may be mounted in any other location. A rain sensor housing 28 forming a partially enclosed space is attached to the front wall 14 by tack welding, for example, around a mounting flange 30. A rain sensor element 32, FIG. 2A, of the rain sensor device 24 is mounted to be protected from non-wind blown rain. The rain sensor element 32 is mounted to a rain sensor housing rear wall 34 which is slanted at an angle Θ between about 45 and 60 degrees from the horizontal line 36. In alternative embodiments, another suitable angle between 0 to 90 degrees may be used. This protects the rain sensor element 32 from raindrops falling vertically and/or when no rain is being drawn into the window fan 10 such as when the window fan 10 is in the exhaust mode.

Alternative locations for the rain sensor device 24 may be directly under the fan opening 17 on the front wall 14 or within the fan housing 12 under the fan 16. The configuration of the rain sensor device 24 as will be described in greater detail below may vary as desired to suit the location of the rain sensor on the housing.

Figure 2A:
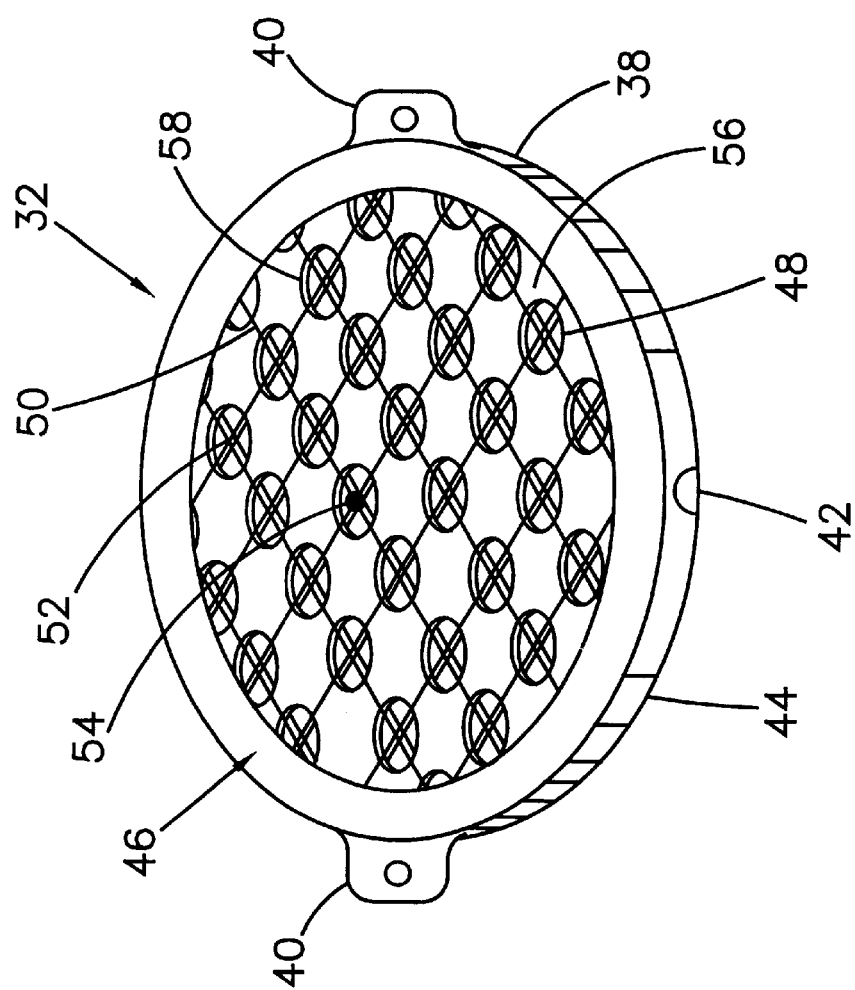
FIG. 2A is a perspective view of a rain sensor device of the window fan of FIG. 1.

The rain sensor element 32, FIG. 2A, has a mount housing 38 with mounting flanges 40 that are mounted to the rain sensor housing rear wall 34. The mount housing 38 has a rain drain 42 on a lower edge 44 which allows any excess water to flow from the rain sensor element 32. This drain 42 insures that if the rain has stopped, a grid work 46, FIG. 2A, will immediately start drying.

The grid work 46 has a lower electrically conductive wire grid 48 with wires crisscrossing in a substantially rectangular pattern although other patterns may be used. An upper electrically conductive wire grid 50 is similarly constructed and is mounted in essentially parallel relationship to the lower grid 48. The crisscrossing wires present a pattern with intersecting points 52 positioned respectively in the lower and upper grids 48 and 50, above each other. The lower and upper grids 48 and 50, respectively, are separated by a predetermined distance of approximately 1/16 inch in the preferred embodiment, this being about the diameter of a rain drop 54. Thus, as rain drop 54 falls through the grid work 46, it will make an electrical contact between the lower and upper grids 48 and 50, respectively. The lower and upper grids 48 and 50 are separated by an insulating plate 56 having a plurality of essentially vertical channels 58 therethrough. The diameter of each channel 58 is approximately 1/4 inch but other dimensions are possible and would make the grid work 46 more sensitive if a larger diameter is used. The intersecting points 52 of the wire grids are positioned substantially in the center of the channels 58 so that as the drop falls through the channel 58, contact will be made therewith. Electrical wires are connected to the lower and upper grids 48 and 50, respectively as will be described below.

Figure 2B:
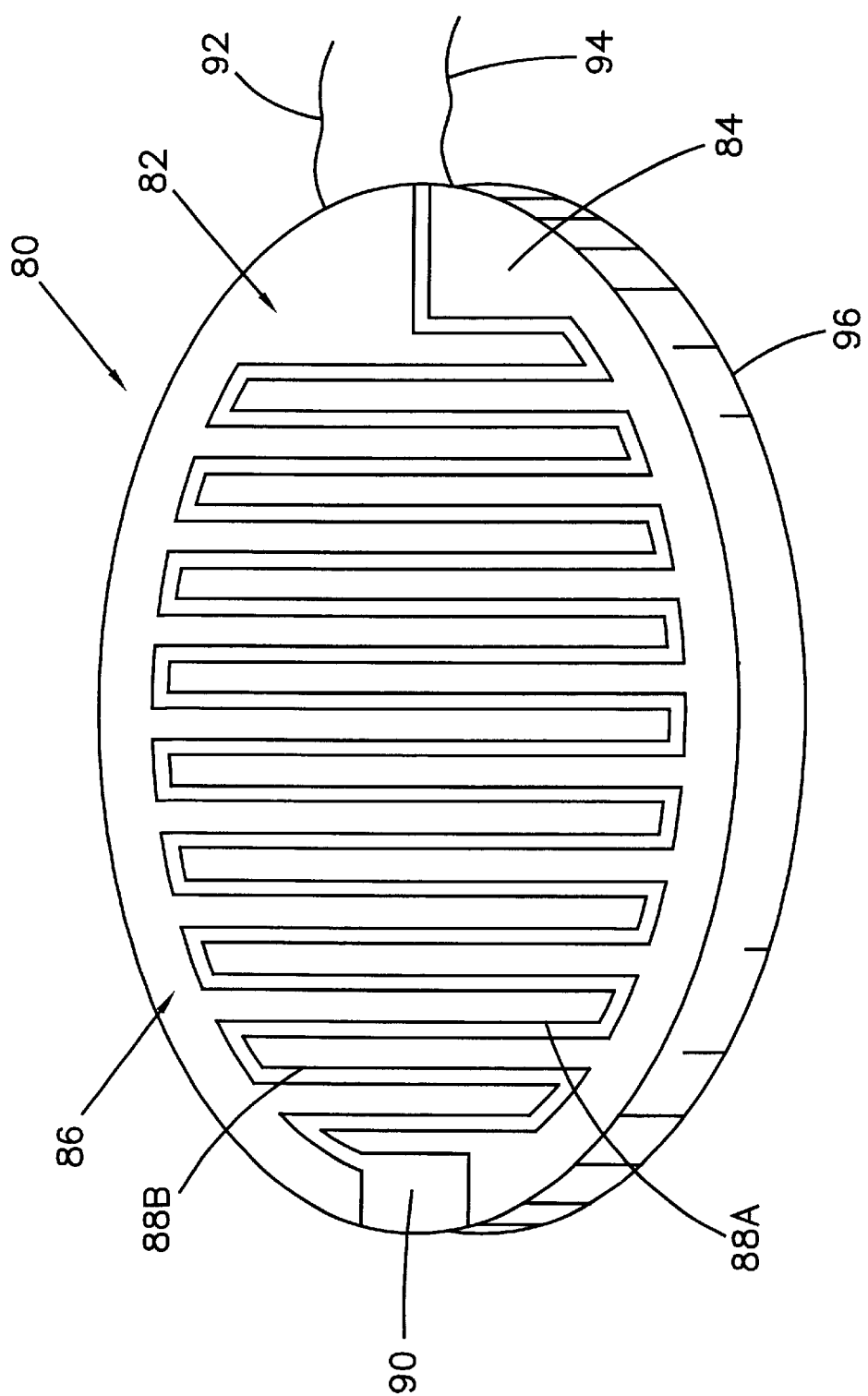
FIG. 2B is a perspective view of another embodiment of a rain sensor element of the window fan in FIG. 1.

FIG. 2B illustrates an alternative embodiment of a sensor element 80. Upon an insulating substrate 96, a first conductive area or track 82 is formed having a plurality of finger-like strips 88A. A second conductive area or track 84 is also formed on the insulative substrate 96 and also has a plurality of finger-like strips 88B. The area where the finger-like strips 88A, 88B of the areas 82 and 84 interface is defined as an interdigitating area 86 where each finger 88A, 88B is separated from the adjacent finger by an insulating strip 90 running therebetween. The width of the insulating strip 90 determines the reactivity of the sensor 80 to rain water. In addition to being electrically insulating, the strip 90 may further be composed of a material which is hydrophobic to water thus insuring that the strip 90 does not remain wet after the raindrop ha s fallen off. The electrical circuit connected to the sensor 80 by wires 92, 94 is detailed below.

If the rain sensor element 32 is located on the housing 12 so that rain carried by the intake air stream whether wind driven or fan drawn will fall on the grid work 46. As noted before, in the event that this rain sensor location is such that the sensor is not directly subject to rain, the grid network may be changed as a result since smaller water drops or mist may be used to activate the grid work 46.

Referring to FIG. 4, an electrical schematic diagram is shown for operating the window fan 10 with the rain sensor element 32 therein.

The rain sensor element 32 has its lower and upper grids 48 and 50, respectively, connected to wires 60 and 62. In its normal electrical state, the rain sensor is an open circuit, but when a raindrop contacts both the lower and upper grids 48 and 50, respectively, the circuit is closed. A manual override switch 64, normally closed, may be used to override the short condition and restart the fan motor(s) 66 if the rain has stopped and the fan motors have not turned on immediately or the operator wants to reverse the direction of the fan 16 to the exhaust mode from the intake mode during rain. The sensor wires 60 and 62 are connected to a controller 68 which may have a relay, normally closed, to provide line power to the fan circuit 70. For example, upon rain, the rain sensor element 32, changing to closed circuit, will cause the relay to open which removes the line power from the fan circuit 70. The lower voltage power is provided to the sensor circuit 72 by a transformer circuit 74. A fan reverse switch 75 is connected in each fan circuit as well as one or more speed control devices 76, one for each fan motor, although one is clearly possible.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. A window fan assembly comprising:
   a housing with openings therein for an air stream through the housing;
   at least one fan mounted to the housing for generating the air stream through the openings of the housing; and
   a sensor connected to the housing, the sensor being disposed on the housing for detecting moisture particles associated with the air stream, upon the detection of a moisture particle of a predetermined size, the sensor causes interruption of the air stream by stopping the fan operation.

2. A window fan assembly in accordance with claim 1 wherein the sensor is mounted in a front wall of the housing or within the housing.

3. A window fan assembly in accordance with claim 2 wherein the sensor is mounted at an angle from about 45 to about 60 degrees from a horizontal axis.

4. A window fan assembly in accordance with claim 1 further including a sensor circuit for controlling the fan operation.

5. A window fan assembly in accordance with claim 4 further comprising an override switch in the sensor circuit to restart the fan operation after interruption by user.

6. A window fan assembly in accordance with claim 4, wherein the sensor comprises a grid work of a pair of conductive elements separated by a predetermined distance.

7. A window fan assembly in accordance with claim 6 wherein the grid work comprises an upper and a lower grid of crisscrossing wires, each grid being connected into the sensor circuit.

8. A window fan assembly in accordance with claim 7 wherein each grid comprises a plurality of crisscrossing wires, the wires crossing at intersecting points.

9. A window fan assembly in accordance with claim 6 wherein the grid work comprises a pair of interdigitating network of conductive finger-like strips, each strip being connected into the sensor circuit, said strips being separated by an insulating strip.

10. A window fan assembly in accordance with claim 7 wherein the grids are separated by an insulative layer having a plurality of channels for the flow of moisture particles therethrough, the moisture particles causing an electrical short between the grids.

11. A window fan assembly in accordance with claim 8 wherein the intersecting points of the upper and lower grids are positioned in the channels.

12. A method of controlling a window fan assembly having at least one fan in a housing with openings therein for an air stream during fan operation, said method comprising the steps of:

mounting a sensor in close proximity to the openings for the air stream for sensing the presence of moisture particles therein;

providing a sensor circuit to control the fan operation;

providing the sensor circuit with a sensor element having two separated conductive grid works, the grid works being separated by a predetermined distance; and in the presence of moisture particles of a predetermined size, the sensor circuit interrupts fan operation to prevent the air stream from carrying the moisture particles through the fan housing.

13. A method of controlling a window fan assembly in accordance with claim 12 further including a switch for restarting the fan after interruption by the user.

14. A method of controlling a window fan assembly in accordance with claim 12 wherein each grid work comprises an upper and lower conductive grid of crisscrossing wires separated by an insulative layer having channels therein.

15. A method of controlling a window fan assembly in accordance with claim 12 wherein the grid work comprises a pair of interdigitating network of conductive finger-like strips, each strip being connected into the sensor circuit, said strips being separated by an insulating strip.

16. A window fan comprising:

a housing configured to fit within a window opening, the housing having at least one air opening with a fan mounted in the housing; and a rain sensor device for controlling the fan in the presence of precipitation, said rain sensor device comprising a rain sensor element having a pair of substantially parallel conductive grids, a lower grid and an upper grid, one above the other, separated by an insulating layer with a plurality of channels therein for allowing moisture particles to pass therethrough, the parallel grids being held a predetermined distance apart by the insulating layer to effect simultaneous contact with the moisture particle of a given diameter and a controller for turning off power to the fan upon at least one moisture particle contacting both the parallel conductive grids.

* * * * *